United States Patent [19]

Haller

[11] Patent Number: 5,327,080
[45] Date of Patent: Jul. 5, 1994

[54] METHOD AND DEVICE FOR NONDESTRUCTIVE TESTING OF A PENETRATION OF A REACTOR PRESSURE VESSEL LID

[75] Inventor: Hans Haller, Mannheim, Fed. Rep. of Germany

[73] Assignee: ABB Reaktor GmbH, Mannheim, Fed. Rep. of Germany

[21] Appl. No.: 19,031

[22] Filed: Feb. 18, 1993

Related U.S. Application Data

[63] Continuation-in-part of Ser. No. 954,383, Sep. 30, 1992.

[30] Foreign Application Priority Data

Nov. 7, 1992 [DE] Fed. Rep. of Germany ....... 4237695

[51] Int. Cl.⁵ .................... G01N 27/82; G01N 27/72; G01R 33/00; G21C 17/00
[52] U.S. Cl. .................................. 324/219; 324/238; 324/262; 376/249
[58] Field of Search ............... 324/219, 220, 221, 237, 324/238, 240, 241, 242, 262; 376/249

[56] References Cited

U.S. PATENT DOCUMENTS 4,757,258 7/1988 Kelly, Jr. et al. .

FOREIGN PATENT DOCUMENTS 3316461 11/1983 Fed. Rep. of Germany .
3411854 10/1984 Fed. Rep. of Germany .

*Primary Examiner*—Walter E. Snow

[57] ABSTRACT

Previously when testing a connector penetration of a reactor pressure vessel lid, one assumed that an annular gap between the connector and the sleeve was concentric. However, tests have shown that in some lid structures a deflection of the connector took place after cooling to room temperature, which led to an eccentric configuration of the sleeve and the connector. In order to be able to completely test such annular gaps, a method and device for nondestructive testing of a penetration of a reactor pressure vessel lid according to the invention includes displacing the sleeve with the help of a thrust piece, until an accessible annular gap is reached. A sensor then arrives at the annular gap through a recess in the thrust piece.

12 Claims, 5 Drawing Sheets

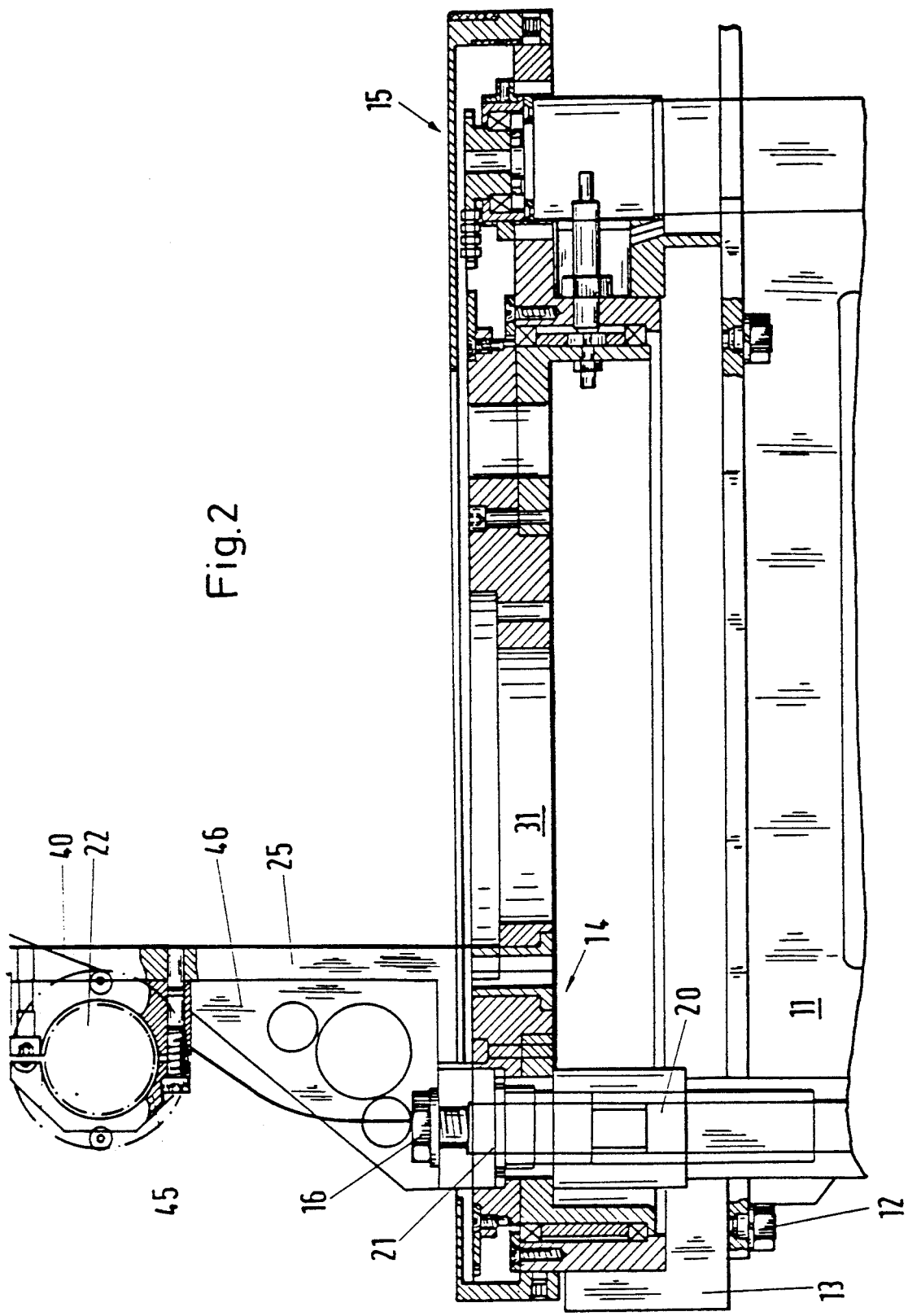

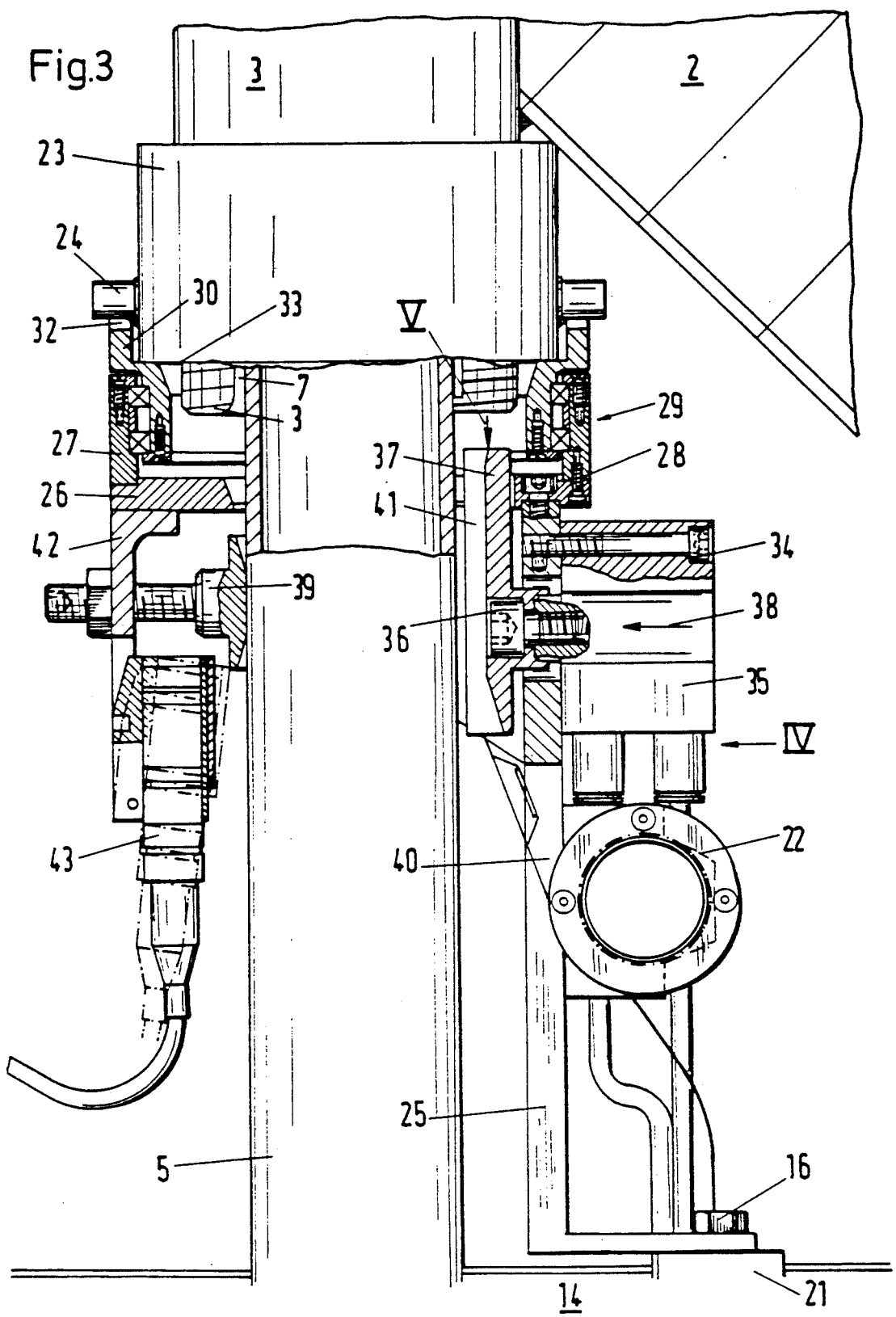

METHOD AND DEVICE FOR NONDESTRUCTIVE TESTING OF A PENETRATION OF A REACTOR PRESSURE VESSEL LID

CROSS-REFERENCE TO RELATED APPLICATION

This application is a Continuation-In-Part of Application Ser. No. 954,383, filed Sep. 30, 1992.

The invention relates to a method and a device for nondestructive testing of a penetration constructed as a welded-in connector of a reactor pressure vessel lid mounted on a depositing ring, wherein the connector is penetrated by a sleeve being retained above the lid, forming an annular gap, a lower end of the sleeve protrudes farther into the interior of the lid than the connector, and a sensor equipped with an eddy current testing head is introduced into the annular gap and moved within it.

Such a testing method, on which U.S. application Ser. No. 954,353, filed Sep. 30, 1992 is based, can be used only if the sleeve is disposed concentrically with the connector.

Some reactor pressure vessel lid structures have the trait of changing their hemispherical shape upon cooling down to room temperature, because of strains in the material. The connectors welded into the lid go along with these changes, and then no longer extend parallel to the axis of the lid. The sleeve, which is fixed in a component of a control rod drive disposed above the connector in such constructions, goes along with this motion only partially if at all, so that a concentric gap between the sleeve and the connector no longer exists. When using the method and device of U.S. application Ser. No. 954,383, filed Sep. 30, 1992, it is no longer possible to carry out testing in regions in which the gap has become too narrow because of the eccentric configuration.

It is accordingly an object of the invention to provide a method and a device for nondestructive testing of a penetration of a reactor pressure vessel lid, which overcome the hereinafore-mentioned disadvantages of the heretofore-known methods and devices of this general type and which enable testing of the entire gap region, even if the sleeve is eccentrically disposed in the connector.

With the foregoing and other objects in view there is provided, in accordance with the invention, in a method for nondestructive testing of a penetration constructed as a welded-in connector of a reactor pressure vessel lid mounted on a depositing ring, including a sleeve being retained above the lid, penetrating the connector, having an axis, and having a lower end protruding farther into the interior of the lid than the connector, and a sensor having an eddy current testing head, the improvement which comprises displacing the sleeve transversely to its axis until reaching a position in which a testable annular gap is attained between the sleeve and the connector, and maintaining the position of the sleeve during a travel motion of the sensor into and within the annular gap.

Testing of the entire gap region can therefore be carried out by traveling in rows along the annular gap.

With the objects of the invention in view, there is also provided in a reactor pressure vessel having a depositing ring; a lid mounted on the depositing ring; a penetration of the lid being constructed as a welded-in connector; a sleeve being retained above the lid, penetrating the connector forming an annular gap between the sleeve and the connector, and having a lower end protruding farther into the interior of the lid than the connector; a frame; fixable floating bearings disposed on the frame; a housing carried by the floating bearings; a turntable disposed on the housing; a manipulator disposed inside the depositing ring for supporting the frame; a vertically adjustable lifting cylinder being associated with the turntable in an eccentric configuration, the lifting cylinder having a piston rod with a free end; an arm being carried by the free end of the piston rod and having an end facing away from the piston rod; and a sensor drive on the arm, a device for nondestructive testing of the penetration, comprising a carrier ring fitting over the sleeve, being secured to the end of the arm facing away from the piston rod and having a top or upper surface; a support ring contacting the connector and being joined or connected to the top or upper surface of the carrier ring; a pneumatic cylinder being carried by the arm, the pneumatic cylinder having a piston penetrating the arm crosswise or transversely to the longitudinal direction, length or extension of the sleeve, the piston of the pneumatic cylinder having a free end; and a thrust piece on the free end of the piston of the pneumatic cylinder.

The support ring serves to support the device, in order to compensate for the force acting relative to the connector upon the sleeve by means of the thrust piece.

In accordance with another feature of the invention, the bearing ring is pressed by a shoulder against an end surface of the connector.

This configuration serves to position the device and given suitable pressure per unit of surface area, it serves to absorb the lateral forces upon displacement of the sleeve by the thrust piece.

In accordance with a further feature of the invention, the support ring fits partway over the connector, and the play between the part of the support ring fitting over the connector and the connector is less than the deflection of a floating bearing.

If the lateral deflection capability of the floating bearing is 5 mm, for instance, then the play between the periphery of the connector and the inner wall of the part of the support ring that clasps the connector must be less than 5 mm, because the overfitting part serves to support the device with respect to the connector during lateral displacement of the sleeve.

With the objects of the invention in view, there is additionally provided in a reactor pressure vessel having a depositing ring; a lid mounted on the depositing ring; a penetration of the lid being constructed as a welded-in connector; a sleeve being retained above the lid, penetrating the connector forming an annular gap between the sleeve and the connector, and having a lower end protruding farther into the interior of the lid than the connector; a frame; fixable floating bearings disposed on the frame; a housing carried by the floating bearings; a turntable disposed on the housing; a manipulator disposed inside the depositing ring for supporting the frame; a vertically adjustable lifting cylinder being associated with the turntable in an eccentric configuration, the lifting cylinder having a piston rod with a free end; an arm being carried by the free end of the piston rod and having an end facing away from the piston rod; and a sensor drive on the arm, a device for nondestructive testing of the penetration, comprising a carrier ring fitting over the sleeve and being secured to the end of the arm facing away from the piston rod, the carrier ring having an upper surface or top; a bearing ring; a support ring being received by the bearing ring, being rotatable relative to the bearing ring, and being joined to the upper surface or top of the carrier ring; bolts projecting from the connector; the support ring having an end facing toward the connector with recesses formed therein laterally fitting over the bolts; a pneumatic cylinder being carried by or joined to the arm, the pneumatic cylinder having a piston penetrating the arm crosswise or transversely to the longitudinal direction, length or extension of the sleeve, the piston of the pneumatic cylinder having a free end; and a thrust piece on the free end of the piston of the pneumatic cylinder.

This version is intended for use of the device at a connector that has laterally projecting bolts. The part of the support ring that clasps the connector serves as a counterpart support for the displacement force exerted by the thrust piece on the sleeve, thereby allowing a sleeve motion that extends relative to the connector to take place. Since the available contact area from the lower edge of the connector to the lower edge of the projecting bolt is too small, the bolts are clasped by the recesses on the end surface of the support ring and the contact area is thereby increased. The rotatability between the bearing ring and the support ring serves to facilitate engagement of the recesses as the support ring moves upward into to its desired position.

In accordance with an added feature of the invention, the pneumatic cylinder is acted upon by variable pressure to actuate the thrust piece.

Since the thrust piece engages at a variable distance from the lid as a function of the semicircular configuration of the lid, due to this provision the compressive force of the pneumatic cylinder can be adjusted in accordance with the necessary bending force.

In accordance with an additional feature of the invention, the thrust piece has a recess extending parallel to the sleeve, for the sensor to be passed through, in order to enable testing of the annular gap region with the thrust piece applied, in which case this region is covered by the thrust piece.

In accordance with a concomitant feature of the invention, there is provided an abutment disposed opposite the thrust piece on the bearing ring, which serves as a stop for the displacement motion of the sleeve. This assures that only a bending moment necessary to form a testable annular gap will act upon the fastening point of the sleeve.

Other features which are considered as characteristic for the invention are set forth in the appended claims.

Although the invention is illustrated and described herein as embodied in a method and a device for nondestructive testing of a penetration of a reactor pressure vessel lid, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

FIG. 2 is an enlarged, fragmentary, sectional view of a portion of a device for carrying out the method;

FIG. 3 is a fragmentary, sectional view of a device for carrying out the method, with portions being broken away and in section;

Figure 1:
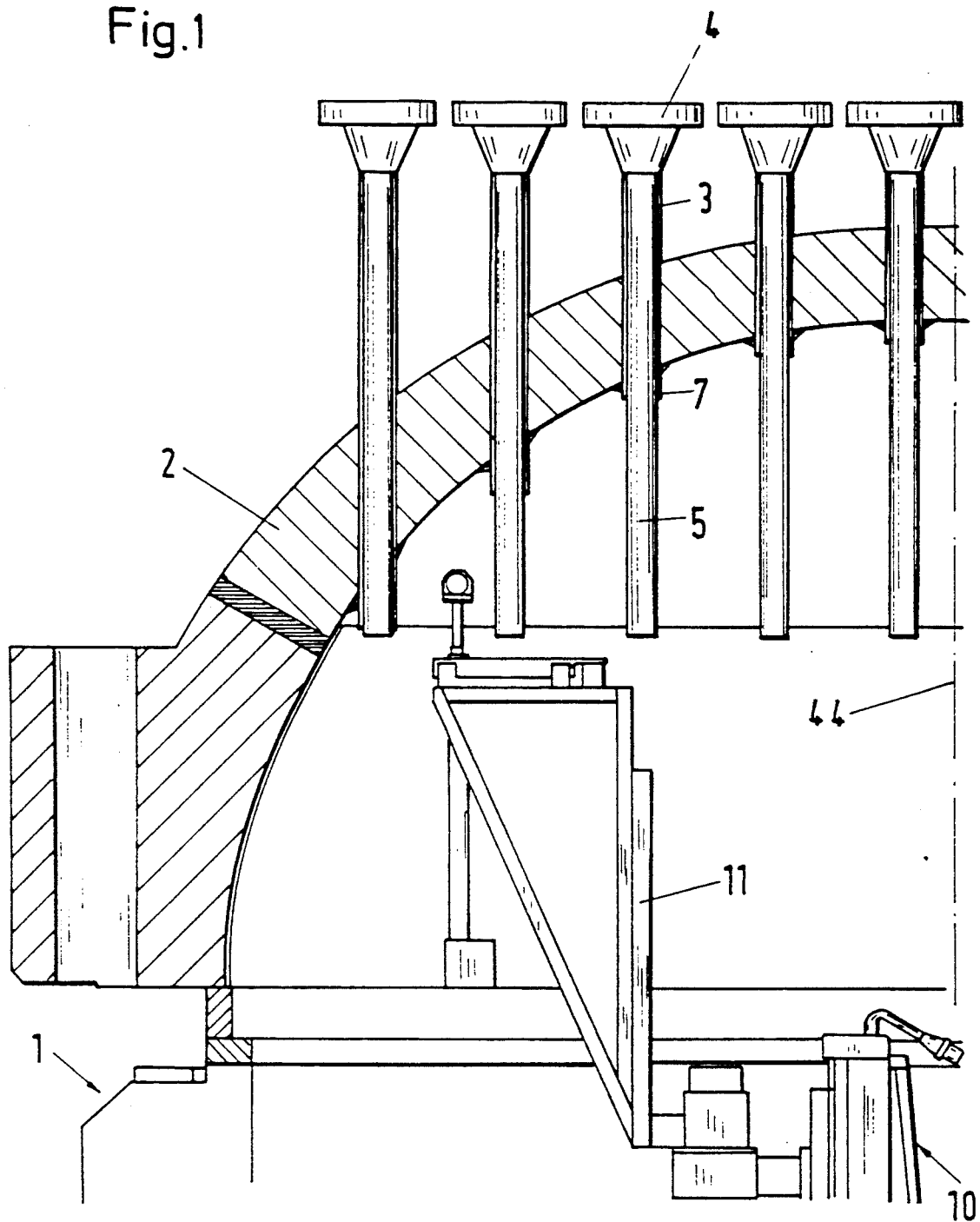
FIG. 1 is a fragmentary, diagrammatic, longitudinal-sectional view of a reactor pressure vessel lid with a diagrammatically illustrated testing device.
Figure 1A:
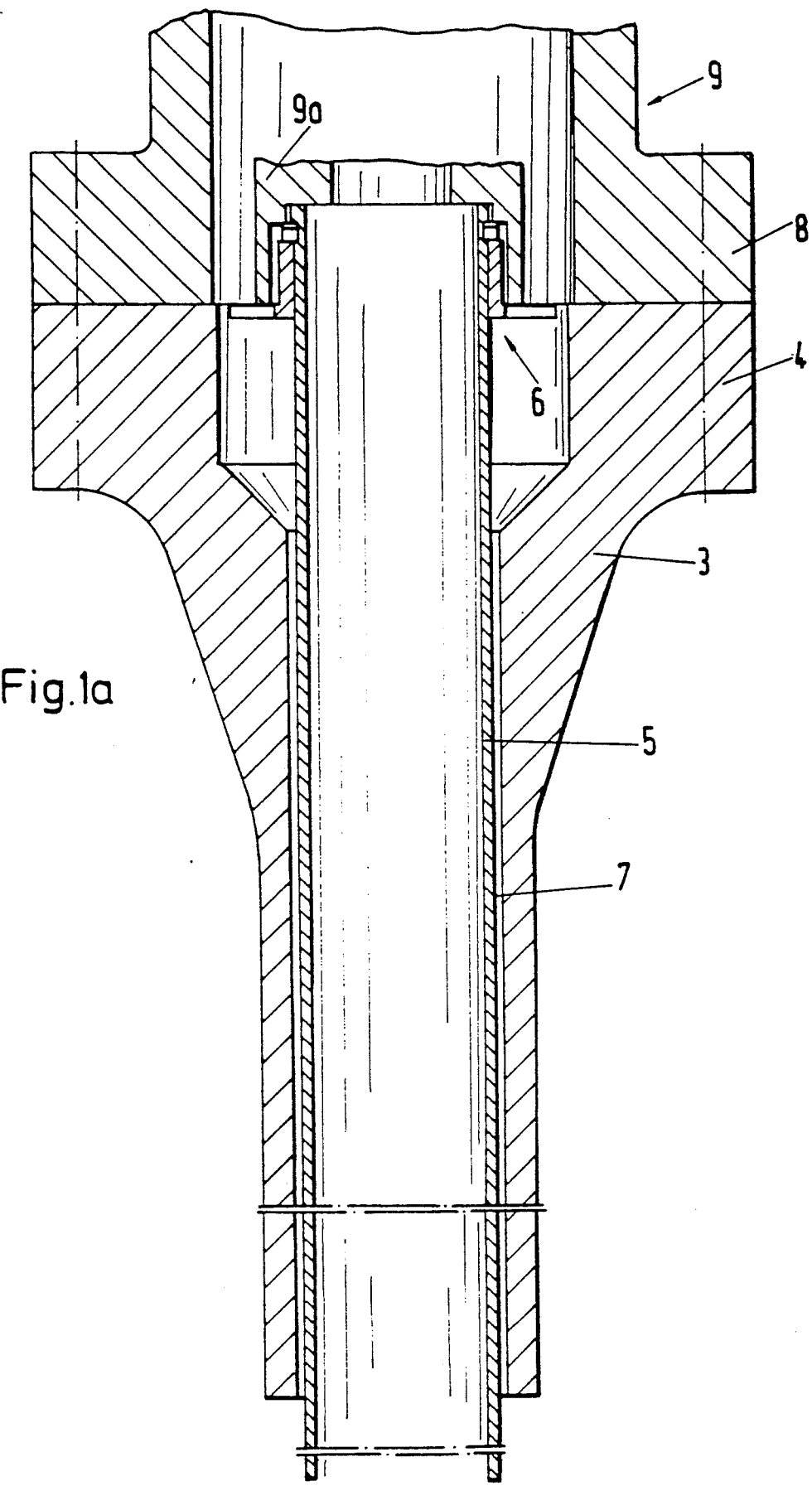
FIG. 1a is an enlarged, fragmentary, longitudinal-sectional view of a connector with a sleeve fixed above it.

Referring now to the figures of the drawing in detail and first, particularly, to FIG. 1 thereof, there is seen a reactor pressure vessel lid 2 which is set on a depositing ring 1. The reactor pressure vessel lid or cover has a plurality of penetrations, lead-throughs or ducts that are constructed as tubular connectors 3 for non-illustrated control rods. The connectors 3 are welded in place in the lid 2 and have ends located outside the lid which diverge conically from one another. As is shown in FIG. 1a, the connectors 3 each merge with a flange 4 for the attachment of a counterpart flange 8 of a control rod drive mechanism or adjusting drive 9. Each respective connector 3 is penetrated by a sleeve 5. As can be seen better from FIG. 1a, each sleeve 5 is secured in a component 9a of the adjusting drive 9 by a clamping device 6, and the sleeve 5 forms an annular gap 7 that is approximately 3 mm in width along with the connector 3. The end of the sleeve 5 toward the interior of the lid protrudes farther into the interior of the lid 2 than the connector 3 by a distance which varies depending on the position of the connector. Strains that are released as the lid 2 cools down cause bulging of the lid, which affects the connector 3 and the sleeve 5 differently, so that an annular gap with a variable eccentricity is formed depending on the position of the connector relative to a center axis 44 of the lid 2. A manipulator 10 disposed in the interior of the depositing ring 1 or the lid 2 has a frame 11. The device described with regard to the subsequent drawing figures for testing the connectors in the region of the annular gap, rests on the frame 11. The manipulator places the frame with parts of the device into a basic position, from which the other components of the device reach a testing position under their own power.

FIG. 2 shows the frame 11, which carries a housing 13 for receiving a turntable or rotary plate 14 through the use of four floating bearings 12. The flat bearings permit a pendulum motion up to a deflection of approximately 5 mm. The turntable 14, which is constructed as a sprocket wheel at its periphery, is set into rotation through a drive unit 15 associated with the housing 13. In an eccentric configuration, the turntable 14 is penetrated by an electromechanical lifting cylinder 20, having a piston rod 21 on which an arm 25 for receiving a sensor drive 22 is pivotably connected. The sensor drive 22 is secured with a clamp retainer 45 that is screwed to the arm 25. A bracket 46 is provided to reinforce the arm 25. The lifting cylinder 20, which is equipped with a drive unit, is secured to the turntable 14 and rotates when the turntable rotates. An end of the connector 3 protruding into the interior of the lid may be constructed in various ways, so that devices that are adapted to it can be used to carry out the method. For instance, the connector 3 in the exemplary embodiment of FIG. 3 is provided on its end protruding into the interior of the lid with an external thread, on which a threaded ring 23 is screwed until it contacts the inside of the lid. Accordingly, the threaded ring 23 is part of the connector 3. Two diametrically opposite bolts 24 that are secured to the periphery of the threaded ring project outward. Other embodiments of the connector end can be seen in FIGS. 6 and 7.

The arm 25 which is joined to the lifting cylinder 20 through a nut 16, serves to receive a carrier ring 26 which clasps the sleeve 5 and is secured to the arm 25 by screws 28. The top of the carrier ring 26 is screwed to a bearing ring 27, which receives a support ring 30 that is rotatable relative to the bearing ring 27, with the interposition of a ball bearing 29. As the device is moved upward with the manipulator 10 shown in FIG. 1, the turntable 14 is penetrated by the sleeve 5, for which purpose a central penetration or duct 31 is provided in the turntable. As is seen in FIG. 3, through the use of the rotatable support of the support ring 30 in the bearing ring 27 and of the floating bearing 12, recesses 32 provided in an end surface of the support ring 30 result in the bolts 24 being clasped or engaged. This process is concluded once there is contact with a shoulder 33 of the threaded ring 23. A variable pneumatic cylinder 35 being acted upon by pressure is secured to the supporting frame 25 with screws 34. A free end of a piston receives a thrust piece or pressure element 37 by using a screw 36. Diagonally opposite the thrust piece 37, an abutment 39 that is adjustable transversely to the sleeve length is associated with the carrier ring 26.

Once the sleeve has been displaced far enough that the approximately concentric annular gap 7 is formed, due to a motion of the thrust piece 37 in the direction of an arrow 38, a sensor 40 which is movable by the sensor drive 22, can be driven into the annular gap. During the motion in the direction of the arrow 38, the deflection motion of the floating bearings 12 also permits an equalization of play until the support ring part that clasps the threaded ring 23 of the connector 3 contacts the jacket surface of the threaded ring. It is not until then that displacement motion of the sleeve 5 relative to the connector 3 begins, and continues until a testable annular gap 7 is reached or until contact is made with the abutment 39 that assures a testable annular gap 7. The annular gap 7 is swept by the sensor 40 in rows, while the guided contact pressure for displacing the sleeve is maintained. A recess 41 in the thrust piece 37 permits introduction of the sensor 40 even once the thrust piece 37 is placed on the sleeve 5. Once one row has been tested, the thrust piece 37 returns to its outset position, so that a rotation of the turntable 14 along with the test device, to the next testing position, can take place. Positioning of the device is performed by observation, using a camera 43 secured to the carrier ring 26 with the interposition of a strap 42.

Figure 4:
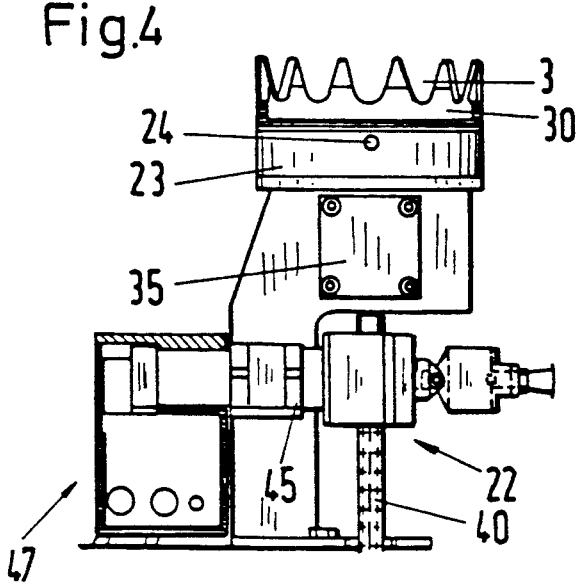
FIG. 4 is a side-elevational view taken along the direction of an arrow IV in FIG. 3.

FIG. 4 is a side view of FIG. 3 which shows the shape of the recesses 32 in the support ring 30 on a smaller scale. The clamp retainer 45 for receiving the sensor drive 22 which can also be seen there, supports the entire drive 22, including a drive motor 47 on the arm 25.

Figure 5:
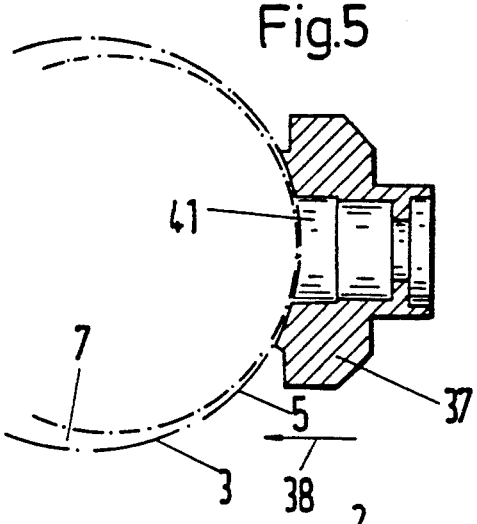
FIG. 5 is a fragmentary, side-elevational view taken along the direction of an arrow V in FIG. 3.

FIG. 5 is a fragmentary view of Fig- 3 which shows the recess 41 in the thrust piece 37 for the passage of the sensor 40 through it. Phantom lines in FIG. 5 also indicate the eccentric disposition of the connector 3 and the sleeve 5, before the eccentric annular gap 7 assumes the concentric form necessary for the testing, due to the motion of the thrust piece 37 in the direction of the arrow 38.

Figure 6:
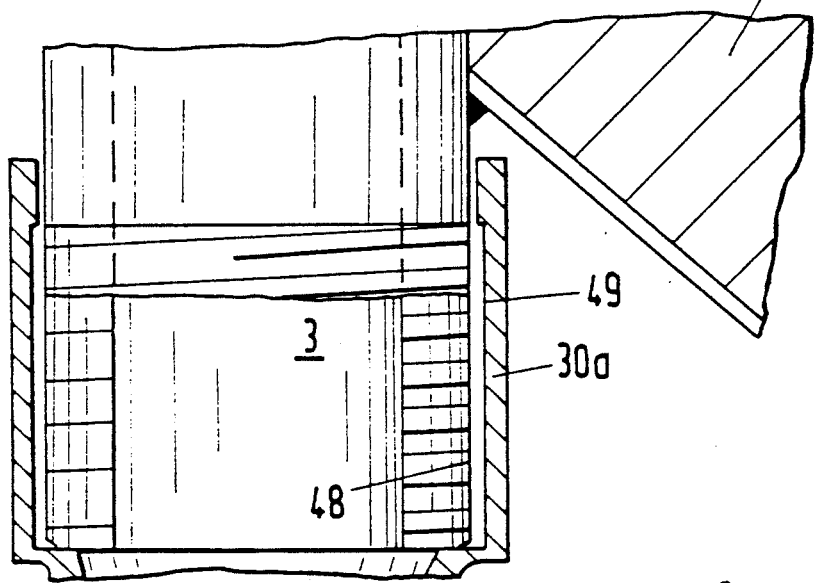
FIG. 6 is a fragmentary view of the device in use, with a different connector embodiment.
Figure 7:
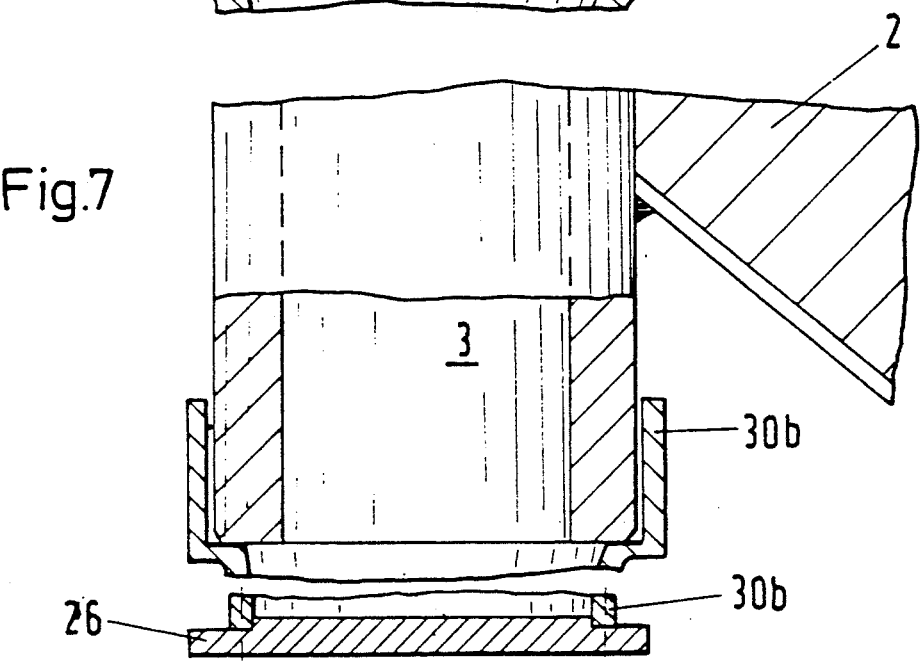
FIG. 7 is a view similar to FIG. 6 of a different device in use with a different connector embodiment.

FIG. 6 shows an end of the connector provided with a thread 48, and FIG. 7 shows a smooth connector end without a thread. To that end, a support ring 30a that has a recessed area 49 in the region of the thread 48 is shown in FIG. 6. When the support ring 30a rests supportingly on the connector 3, the thread 48 is not damaged.

In the version of FIG. 7, a low height of a portion of a support ring 30b fitting over the connector 3 suffices to achieve an adequate counterpart bearing for the displacement motion of the sleeve 5. As FIG. 7 shows, the support ring 30b is joined directly to the carrier ring 26. This embodiment can also be used in FIG. 6, since in FIG. 6 as well, the absence of bolts 24 means that rotatability of the support ring 30a is not necessary.

I claim:

1. In a method for nondestructive testing of a penetration constructed as a welded-in connector of a reactor pressure vessel lid mounted on a depositing ring, including a sleeve being retained above the lid, penetrating the connector, having an axis, and having a lower end protruding farther into the interior of the lid than the connector, and a sensor having an eddy current testing head, the improvement which comprises displacing the sleeve transversely to its axis until reaching a position in which a testable annular gap is attained between the sleeve and the connector, and maintaining the position of the sleeve during a travel motion of the sensor into and within the annular gap.

2. In a reactor pressure vessel having a depositing ring; a lid mounted on the depositing ring; a penetration of the lid being constructed as a welded-in connector; a sleeve being retained above the lid, penetrating the connector forming an annular gap between the sleeve and the connector, and having a lower end protruding farther into the interior of the lid than the connector; a frame; fixable floating bearings disposed on the frame; a housing carried by the floating bearings; a turntable disposed on the housing; a manipulator disposed inside the depositing ring for supporting the frame; a vertically adjustable lifting cylinder being associated with the turntable in an eccentric configuration, the lifting cylinder having a piston rod with a free end; an arm being carried by the free end of the piston rod and having an end facing away from the piston rod; and a sensor drive on the arm, a device for nondestructive testing of the penetration, comprising a carrier ring fitting over the sleeve, being secured to the end of the arm facing away from the piston rod and having an upper surface; a support ring contacting the connector and being joined to the upper surface of said carrier ring; a pneumatic cylinder being carried by the arm, said pneumatic cylinder having a piston penetrating the arm transversely to the longitudinal direction of the sleeve, said piston of said pneumatic cylinder having a free end; and a thrust piece on the free end of said piston of said pneumatic cylinder.

3. The device according to claim 2, wherein the connector has an end surface, and said support ring has a shoulder being placed against the end surface of the connector.

4. The device according to claim 2, wherein one of the floating bearings has a given deflection; said support ring partly clasps the connector; and said support ring has a part fitting over the connector with play between the part of said support ring fitting over the connector and the connector being less than the given deflection.

5. The device according to claim 2, including means for acting upon said pneumatic cylinder with variable pressure.

6. The device according to claim 2, wherein said thrust piece has a recess formed therein extending parallel to the sleeve.

7. The device according to claim 2, including an adjustable abutment disposed on said carrier ring diametrically opposite the thrust piece.

8. In a reactor pressure vessel having a depositing ring; a lid mounted on the depositing ring; a penetration of the lid being constructed as a welded-in connector; a sleeve being retained above the lid, penetrating the connector forming an annular gap between the sleeve and the connector, and having a lower end protruding farther into the interior of the lid than the connector; a frame; fixable floating bearings disposed on the frame; a housing carried by the floating bearings; a turntable disposed on the housing; a manipulator disposed inside the depositing ring for supporting the frame; a vertically adjustable lifting cylinder being associated with the turntable in an eccentric configuration, the lifting cylinder having a piston rod with a free end; an arm being carried by the free end of the piston rod and having an end facing away from the piston rod; and a sensor drive on the arm, a device for nondestructive testing of the penetration, comprising a carrier ring fitting over the sleeve and being secured to the end of the arm facing away from the piston rod, said carrier ring having an upper surface; a bearing ring; a support ring being received by said bearing ring, being rotatable relative to said bearing ring, and being joined to the upper surface of said carrier ring; bolts projecting from the connector; said support ring having an end facing toward the connector with recesses formed therein laterally fitting over said bolts; a pneumatic cylinder being carried by the arm, said pneumatic cylinder having a piston penetrating the arm transversely to the longitudinal direction of the sleeve, said piston of said pneumatic cylinder having a free end; and a thrust piece on the free end of said piston of said pneumatic cylinder.

9. The device according to claim 8, wherein one of the floating bearings has a given deflection; said support ring partly clasps the connector; and said support ring has a part fitting over the connector with play between the part of said support ring fitting over the connector and the connector being less than the given deflection.

10. The device according to claim 8, including means for acting upon said pneumatic cylinder with variable pressure.

11. The device according to claim 8, wherein said thrust piece has a recess formed therein extending parallel to the sleeve.

12. The device according to claim 8, including an adjustable abutment disposed on said carrier ring diametrically opposite the thrust piece.

* * * * *